United States Patent

Butera et al.

Patent Number: 5,206,252
Date of Patent: Apr. 27, 1993

[54] THIADIAZOLYL-AMINO DERIVATIVES OF BENZOPYRANS AND INDANES

[75] Inventors: John A. Butera, Kendall Park; Jehan F. Bagli, Princeton, both of N.J.

[73] Assignee: American Home Products Corporation, New York, N.Y.

[21] Appl. No.: 880,433

[22] Filed: May 8, 1992

[51] Int. Cl.$^5$ ............... C07D 417/12; C07D 285/10; A61K 31/41
[52] U.S. Cl. ..................... 514/362; 548/135
[58] Field of Search ................ 548/135; 514/362

[56] References Cited

U.S. PATENT DOCUMENTS 4,692,531 9/1987 Algieri ........................ 548/193
4,782,083 11/1988 Cassidy ....................... 514/456

FOREIGN PATENT DOCUMENTS 399834 11/1990 opean Pat. Off. .
426379  5/1991 opean Pat. Off. .
2204868 11/1988 United Kingdom .

OTHER PUBLICATIONS

Longman et al., Medicinal Research Reviews, 1992, 12, 73.
Robertson, et al., J. Med. Chem, 1990, 33, 1529.
Weston, et al., TiPS, 1990, 11, 417.
Evans et al., Ann. Rep. Med. Chem., 1991, 26, 73.

Primary Examiner—Robert Gerstl
Attorney, Agent, or Firm—Richad K. Jackson

[57] ABSTRACT

The compounds of the formula:

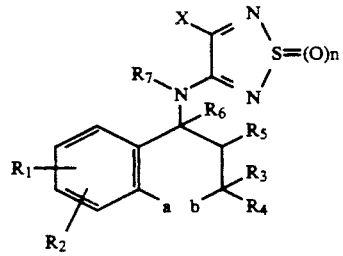

wherein $R_1$ and $R_2$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, $C_{2-12}$ mono- or di-alkylcarbamoyl, or hydrogen; a and b together form an —O— linkage or a direct bond; $R_3$ and $R_4$, independent from each other, are $C_{1-6}$ alkyl when a and b form an —O— linkage or, H or $C_{1-6}$ alkyl when a and b form a direct bond; either $R_5$ is hydrogen, hydroxyl, $C_{2-6}$ alkanoyloxy, $C_{7-12}$ aroyloxy, carbamoyloxy, formyloxy, $C_{2-6}$ alkoxycarbonyloxy, mono or di $C_{2-12}$ alkylcarbamoyloxy, and $R_6$ is hydrogen, or $R_5$ and $R_6$ together are a bond; $R_7$ is hydrogen, $C_{1-6}$ alkyl, $C_{1-6}$ alkanocarbonyl, or $C_{16}$ alkanosulfonyl; X is selected from the following: —$NR_8R_9$, wherein $R_8$ and $R_9$, independent from each other are hydrogen, $C_{1-6}$ alkyl, $C_{2-6}$ alkylcarbonyl, $C_{7-12}$ arylalkyl, thienylmethyl, pyridinylmethyl, piperazinylmethyl, or pyrimidinylmethyl, or $R_8$ and $R_9$ taken together are polymethylene of 3-10 carbon atoms or $R_8$ and $R_9$ taken with the nitrogen atom to which they are attached complete a piperazine, morpholine, pyrroline, pyrrolidinone, imidazole, imidazolone, piperidine or piperidinone ring structure; or —$OR_{10}$, wherein $R_{10}$ is hydrogen, $C_{1-6}$ alkyl or $C_{2-6}$ alkylcarbonyl; and n is an integer from 0–2; or a pharmaceutically acceptable salt thereof, are useful antihypertensive, K channel activators.

18 Claims, No Drawings

THIADIAZOLYL-AMINO DERIVATIVES OF BENZOPYRANS AND INDANES

BACKGROUND OF THE INVENTION

The present invention relates to novel benzopyrans and indans having pharmacological activity, to a process for preparing them, to pharmaceutical compositions containing them, and to their use in the treatment of hypertension and urinary incontinence via potassium channel modulation.

Recent reviews of potassium channel modulators are by: Longman et al., *Medicinal Research Reviews*, 1992, 12, 73; Robertson et al.; *J. Med. Chem.* 1990, 33, 1529; Weston et al.; *TiPS* 1990, 11, 417; and Evans et al., *Ann. Rep. Med. Chem.* 1991, 26, 73. Stemp et al. disclose a class of cyclobutenedione derivatives of chromans described as having blood pressure lowering activity and bronchodilatory activity in European Patent Application EP-426379-A2. The same group discloses a related class of 1,2,4-triazole derivatives as having similar blood pressure lowering and bronchodilatory activity in European Patent Application EP-399834-A2. In addition, Blarer discloses a related class of substituted chromans useful for treatment of raised blood pressure and smooth muscle tension in UK Patent Application GB-2204868-A.

DESCRIPTION OF THE INVENTION

Accordingly, the present invention provides [1,2,5] thiadiazole derivatives represented by formula (I):

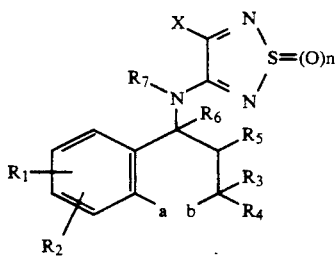

wherein:

$R_1$ and $R_2$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, $C_{2-12}$ mono- or di-alkylcarbamoyl, or hydrogen;

a and b together form an —O— linkage or a direct bond;

$R_3$ and $R_4$, independent from each other, are $C_{1-6}$ alkyl when a and b form an —O— linkage or, H or $C_{1-6}$ alkyl when a and b form a direct bond;

either $R_5$ is hydrogen, hydroxyl, $C_{2-6}$ alkanoyloxy, $C_{7-12}$ aroyloxy, carbamoyloxy, formyloxy, $C_{2-6}$ alkoxycarbonyloxy, mono or di $C_{2-12}$ alkylcarbamoyloxy, and $R_6$ is hydrogen, or $R_5$ and $R_6$ together are a bond;

$R_7$ is hydrogen, $C_{1-6}$ alkyl, $C_{1-6}$ alkanocarbonyl, or $C_{1-6}$ alkanosulfonyl;

X is selected from the following:

—$NR_8R_9$, wherein $R_8$ and $R_9$, independent from each other are hydrogen, $C_{1-6}$ alkyl, $C_{2-6}$ alkylcarbonyl, $C_{7-12}$ arylalkyl, thienylmethyl, pyridinylmethyl, piperazinylmethyl, or pyrimidinylmethyl, or $R_8$ and $R_9$ taken together are polymethylene of 3-10 carbon atoms or $R_8$ and $R_9$ taken with the nitrogen atom to which they are attached complete a piperazine, morpholine, pyrrolidine, pyrrolidinone, imidazole, imidazolone, piperidine or piperidinone ring structure;

or —$OR_{10}$, wherein $R_{10}$ is hydrogen, $C_{1-6}$ alkyl or $C_{2-6}$ alkylcarbonyl; and n is an integer from 0-2;

or a pharmaceutically acceptable salt thereof.

The most preferred compounds are represented by formula (I) wherein:

$R_1$ and $R_2$, independent from each other, are trifluoromethoxy, methoxy, nitro, cyano, chloro, bromo, fluoro, trifluoromethyl, methanesulfonamido, $C_{1-3}$ alkyl, $C_{1-6}$ mono or di-alkylamino, acetamido, trifluoroacetamido, or trifluoromethanesulfonamido;

a and b together form an —O— linkage or a direct bond;

$R_3$ and $R_4$ are methyl when a and b form an —O— linkage or, H or methyl when a and b form a direct bond;

either $R_5$ is hydrogen, or hydroxyl, and $R_6$ is hydrogen, or $R_5$ and $R_6$ together form a bond;

$R_7$ is hydrogen or methyl;

X is $NR_8R_9$, wherein $R_8$ and $R_9$, independent from each other, are, hydrogen, $C_{1-3}$ alkyl, $C_{7-12}$ arylalkyl or thienylmethyl, or $R_8$ and $R_9$ together are polymethylene of 4 to 6 carbon atoms, or $R_8$ and $R_9$ taken together with the nitrogen atom to which they are attached complete a pyrrolidine, pyrrolidinone, piperazine, piperidine or piperidinone ring structure; and n is an integer from 1-2;

or a pharmaceutically acceptable salt thereof.

It is understood that the definition of the compounds of formula (I) when $R_5$ is hydrogen or hydroxy and $R_6$ is hydrogen encompasses all possible stereoisomers and mixtures thereof. In particular, it encompasses racemic modifications and any optical isomers. Optical isomers may be obtained in pure form by standard separation techniques. The pharmaceutically acceptable salts of these compounds are prepared by reaction of the free compound of formula (I) with organic or inorganic acids or bases. The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids. Where $R_1$ and/or $R_2$ are carboxyl groups, or $R_7$ is a proton, salts of the compounds of this invention may be formed with bases such as the alkali metals (Na, K, or Li) or the alkaline earth metals (Ca or Mg).

The present invention also provides a process for the preparation of a compound of formula (I). More particularly, the compounds of formula (I) wherein $R_5$ is hydroxy and $R_6$ is hydrogen may be prepared by one of the following processes:

a) reacting a compound of formula (II):

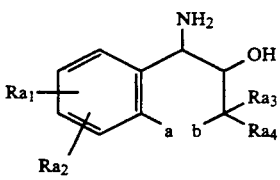

wherein Ra₁, Ra₂, Ra₃, and Ra₄ are R₁, R₂, R₃, and R₄, respectively as defined hereinbefore or a group or atom convertible thereto, with a compound of formula (III):

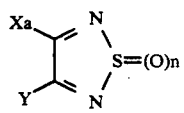

wherein Xa is X as defined hereinbefore or a group or atom convertible thereto, Y is an appropriate leaving group such as $C_{1-6}$ alkoxy or halogen, and n is an integer from 0–2; in a solvent such as an alcohol or acetonitrile, to give compounds of formula (I) with $R_5$=hydroxy and $R_6$=H.

b) reacting a compound of formula (IV):

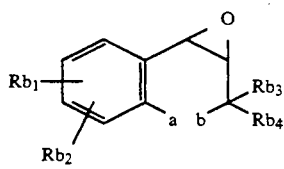

wherein Rb₁, Rb₂, Rb₃, and Rb₄, and R₁, R₂, R₃, and R₄, respectively, as defined hereinbefore or a group or atom convertible thereto, with a compound of formula (V):

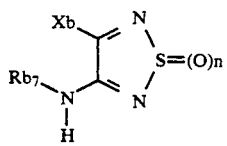

wherein Xb is X as defined herein before or a group or atom convertible thereto, Rb₇ is R₇ as defined hereinbefore or a group or atom convertible thereto, and n is an integer from 0–2. It is particularly preferred that the reaction between the compound of formula (IV) and (V) is conducted under basic conditions so as to facilitate the formation of the anion of (V), for example, in the presence of sodium hydride in tetrahydrofuran or dimethylformamide, to give compounds of formula (I) with $R_5$=hydroxy and $R_6$=H.

Using either process, the compound of formula (I) wherein R₅ is hydroxy and R₆ is hydrogen may be optionally dehydrated according to methods known in the art of organic synthesis to give a compound of formula (I) wherein R₅ and R₆ together are a bond. The compound of formula (I) wherein R₅ is hydroxy and R₆ is hydrogen may be optionally de-oxygenated according to methods known in the art of organic synthesis to give a compound of formula (I) wherein R₅ and R₆ are both hydrogen.

As mentioned previously, the compounds of formula (I) have been found to have blood pressure lowering activity. They are therefore useful in the treatment of hypertension. Furthermore, the compounds of formula (I) are active as potassium channel activators which render them useful for treatment of peripheral vascular disease, congestive heart failure, stroke, anxiety, cerebral anoxia and other neurodegenerative disorders, disorders involving excessive smooth muscle contraction of the urinary tract (such as incontinence), or of the gastro-intestinal tract (such as irritable bowel syndrome), asthma, and hair loss.

The present invention accordingly provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure and in the form of an aerosol for intrabronchial administration to asthmatics.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the treatment of hypertension and/or smooth muscle relaxation.

The present invention further provides a method of treating hypertension in mammals including man, which comprises administering to the afflicted mammal an antihypertensive effective amount of a compound or a pharmaceutical composition of the invention.

The following examples are presented to illustrate rather than limit the methods for production of representative compounds of the invention.

EXAMPLE 1

(−)-(3S,4R)-4-(4-Ethoxy-1,1-dioxo-[1,2,5]thiadiazol-3-ylamino)-2,2-dimethyl-6-trifluoromethoxy-chroman-3-ol

Step 1) Preparation of 3,4-Diethoxy-[1,2,5]thiadiazole-1,1-dioxide.

The compound was prepared according to Carmack et al. (*J. Org. Chem.* 1975, 40, 2743) as follows. Potassium metal (10.0 g, 0.26 mol) was dissolved in cool isopropanol (50 mL) which was then diluted with methanol (50 mL). A methanolic solution (100 mL) of sulfamide (12.32 g, 0.13 mol) was added dropwise with vigorous stirring, followed by dropwise diethyl oxalate (17.4 mL, 0.13 mol). The resulting mixture was heated at reflux for 18 hours. The mixture was cooled, filtered, and the solid was washed with methanol and dried to give 28.3 g of 3,4-dihydroxy-[1,2,5]thiadiazole-1,1-dioxide as the di-potassium salt. This was stirred with $PCl_5$ (90.0 g, 0.43 mol) at 150° C. for 10 minutes. When enough $POCl_3$ was generated to maintain stirring, the mixture was cooled to 60° C. and stirred for 18 hours. The reaction was cooled, diluted with diethyl ether, filtered, and washed with additional diethyl ether. The ether filtrate was added dropwise to ethanol (500 mL) at 0° C. The resulting solution was heated to reflux for 1.5 hours, cooled, and concentrated to ¼ volume. The diethoxy derivative was collected as a white solid (4.80 g). The mother liquor afforded an additional 1.80 g. (Total yield: 26%): mp 171°–172° C. (Th. 178°–179° C.); $^1$H NMR ($CDCl_3$): δ 4.59 (q, 4H), 1.50 (t, 6H).

Step 2) Preparation of (−)-(3S, 4R)-4-(4-Ethoxy-1,1-dioxo-[1,2,5]thiadiazol-3-ylamino)-2,2-dimethyl-6-trifluoromethoxy-chroman-3-ol (3S, 4R)-4-Amino-2,2-dimethyl-6-(trifluoromethoxy)-chroman-3-ol [prepared by the method of Quagliato et al. *Biorg. and Med. Chem. Let.* 1991, 1, 39; (1.00 g, 3.61 mmol)] and the thiadiazole derivative (0.78 g, 3.79 mmol) obtained in Step 1 were stirred together in acetonitrile (15 mL) at 90° C. for 18 hours. The mixture was cooled and concentrated, and the residue was purified by column chromatography (1:1:05 hexane/ethyl acetate/dichloromethane) to give after trituration with hexanes 1.10 g (71%) of product as a white solid: mp 192°–194° C.; $^1$H NMR (DMSO-$D_6$): δ 9.55 (d, 1H), 7.29 (d, 1H), 7.19 (d, 1H), 6.87 (d, 1H), 5.89 (d, 1H), 4.73 (t, 1H), 4.51 (q, 2H), 3.78 (m, 1H), 1.41 (t, 3H), 1.38 (s, 3H), 1.15 (s, 3H); IR (KBr): 2500–3250, 1620, 1490 cm$^{-1}$; MS (m/z) 438 (MH$^+$, 100%), 261 (20).

Elemental analysis for $C_{16}H_{18}N_3O_6SF_3$: Calc'd: C, 43.94; H, 4.15; N, 9.61. Found: C, 43.63; H, 4.26, N, 9.00.

EXAMPLE 2

(−)-(3S,4R)-4-(4-Amino-1,1-dioxo-[1,2,5]thiadiazol-3-ylamino)2,2-dimethyl-6-trifluoromethoxy-chroman-3-ol The product of Example 1, Step 2 (0.200 g, 0.458 mmol) was dissolved in acetonitrile (10 mL) at 0° C. Ammonia gas was bubbled through using a scintered glass tube for 30 minutes. The reaction was warmed to 25° C., capped, and stirred overnight. The solvent was removed by vacuum and the residue was triturated with diethyl ether/hexane to give 0.150 g (80%) of product as a white solid: mp 279°–281° C.; $^1$H NMR (DMSO-$D_6$): δ 9.00 (br s, 1H), 8.94 (d, 1H), 7.82 (br s, 1H), 7.23 (m, 2H), 6.90 (d, 1H), 6.00 (d, 1H), 4.77 (t, 1H), 3.63 (dd, 1H), 1.40 (s, 3H), 1.19 (s, 3H); IR (KBr): 3360, 1605, 1630, 1690 cm−1; MS (m/z) 409 (MH$^+$, 40%).

Elemental analysis for $C_{14}H_{15}N_4O_5SF_3$: Calc'd: C, 41.18; H, 3.70: N, 13.72. Found: C, 41.03; H, 3.63; N, 13.38.

EXAMPLE 3

(−)-(3S,4R)-2,2-Dimethyl-4-(4-methylamino-1,1-dioxo-[1,2,5]-thiadiazol-3-ylamino)-6-trifluoromethoxy-chroman-3-ol The product of Example 1, Step 2 (0.200 g, 0.458 mmol) in acetonitrile (5 mL) at 0° C. was treated with methylamine gas for 10 minutes. The mixture was stirred for 1 hour at 25° C. The solvent was removed and the residue was triturated with diethyl ether/hexane to give 0.17 g (88%) of product as a white solid: mp 280–282 (dec); $^1$H NMR (DMSO-$D_6$): δ 8.82 (br s, 1H), 8.50 (br s, 1H), 7.25 (s, 1H), 7.21 (d, 1H), 6.89 (d, 1H), 5.96 (br m, 1H), 4.76 (d, 1H), 3.61 (d, 1H), 2.94 (s, 3H), 1.39 (s, 3H), 1.19 (s, 3H); IR (KBr) 3360, 1625 cm$^{-1}$; MS (m/z) 423 (MH$^+$, 40%), 361 (23), 163 (60).

Elemental analysis for $C_{15}H_{17}N_4O_5SF_3$: Calc'd: C, 42.65; H, 4.06; N, 13.26. Found: C, 42.52; H, 4.09; N, 13.01.

EXAMPLE 4

(−)-(3S,4R)-2,2-Dimethyl-4-(4-dimethylamino-1,1-dioxo-[1,2,5]-thiadiazol-3-ylamino)-6-trifluoromethoxy-chroman-3-ol In a method similar to Example 3, the product of Example 1, Step 2 (0.250 g, 0.572) was converted to the title compound with dimethylamine gas to give, after recrystallization from diethyl ether/hexane, 0.19 g (76%) of product as a white solid: mp 135°–140° C.; $^1$H NMR (DMSO-$D_6$): δ 8.09 (br s, 1H), 7.23 (br s, 1H), 7.10 (d, 1H), 6.82 (d, 1H), 5.84 (br s, 1H), 4.77 (m, 1H), 3.75 (m, 1H), 3.35 (s, 3H), 2.53 (s, 3H), 1.38 (s, 3H), 1.19 (s, 3H); IR (KBr): 3400, 1600 cm$^{-1}$; MS (m/z) 437 (MH$^+$, 100%), 419 (65), 245 (35) 177 (70); $[\alpha]_D^{25} = -85.4$ (THF).

Elemental analysis for $C_{16}H_{19}N_4O_5SF_3$: Calc'd: C, 44.03; H, 4.39; N, 12.84. Found: C, 44.28; H, 4.72; N, 13.19.

EXAMPLE 5

(−)-(3S,4R)-4-(4-Benzylamino-1,1-dioxo-[1,2,5]thiadiazol-3-ylamino)-2,2-dimethyl-6-trifluoromethoxy-chroman-3-ol To the product of Example 1, Step 2 (0.250 g, 0.572 mmol) stirring in acetonitrile (2 mL) was added benzylamine (0.07 mL, 0.629 mmol). The mixture stirred at 25° C. for 18 hours and was concentrated to afford a residue which was recrystallized from diethyl ether/hexane to give 0.17 g (60%) of product as a white solid: mp 274°–276° C. (dec); $^1$H NMR (DMSO-$D_6$): δ 8.95 (br s, 1H), 8.75 (br s, 1H), 7.42 (m, 5H), 7.29 (s, 1H), 7.20 (d, 1H), 6.89 (d, 1H), 5.99 (br s, 1H), 4.80 (br d, 1H), 4.56 (s, 2H), 3.59 (d, 1H), 1.39 (s, 3H), 1.19 (s, 3H); IR (KBr): 3300, 1620 cm$^{-1}$; MS (m/z) 499 (MH$^+$, 100%); $[\alpha]_D^{25} = -45.4$ (THF).

Elemental analysis for $C_{21}H_{21}N_4O_5SF_3$: Calc'd: C, 50.60; H, 4.25; N, 11.24. Found: C, 50.51; H, 4.22; N, 11.11.

EXAMPLE 6

(−)-(3S,4R)-4-[1,1-Dioxo-4-(4-trifluoromethylbenzylamino)-[1,2,5]-thiadiazol-3-ylamino]-2,2-dimethyl-6-trifluoromethoxy-chroman-3-ol In a method similar to Example 5, the product of Example 1, Step 2 (0.250 g, 0.572 mmol) was converted to the title compound with 4-(trifluoromethyl)benzylamine (0.09 mL, 0.629 mmol) to afford 0.25 g (77%) of product as a white solid: mp 283°–284° C.; $^1$H NMR (DMSO-D$_6$): δ 8.94 (d, 1H), 8.92 (t, 1H), 7.78 (d, 2H), 7.64 (d, 2H), 7.32 (d, 1H), 7.21 (dd, 1H), 6.90 (d, 1H), 6.00 (d, 1H), 4.80 (t, 1H), 4.62 (d, 2H), 3.62 (m, 1H), 1.40 (s, 3H), 1.20 (s, 3H); IR (KBr) 3300, 1610 cm$^{-1}$; MS (m/z) 567 (MH$^+$, 100%); [α]$_D^{25}$ = −44.8 (THF).

Elemental analysis for C$_{22}$H$_{20}$N$_4$O$_5$SF$_6$: Calc'd: C, 46.65; H, 3.56; H, 9.89. Found: C, 46.73; H, 3.60; H, 9.60.

EXAMPLE 7

(−)-(3S,4R)-4-[4-(1-methylethylamino)-1,1-dioxo-[1,2,5]thiadiazol-3-ylamino]-2,2-dimethyl-6-(trifluoromethoxy)-chroman-3-ol In a method similar to Example 5, the product of Example 1, Step 2 (0.200 g, 0.457 mmol) was converted to the title compound with isopropylamine (0.64 mL, 7.5 mmol) in 1 hour to give 0.180 g (87%) of a white solid: mp 296–298 (dec); $^1$H NMR (DMSO-D$_6$): δ 8.90 (br s, 1H), 8.30 (br s, 1H), 7.26 (s, 1H), 7.23 (d, 1H), 6.91 (d, 1H), 6.00 (d, 1H), 4.78 (d, 1H), 3.86 (br t, 1H), 3.63 (dd, 1H), 1.40 (s, 3H), 1.24 (dd, 6H), 1.16 (s, 3H); IR (KBr) 3300, 1620 cm$^{-1}$; MS (m/z) 451 (MH$^+$, 100%); [α]$_D^{25}$ = −73.5 (THF)

Elemental analysis for C$_{17}$H$_{21}$N$_4$SO$_5$F$_3$: Calc'd: C, 45.33; H, 4.70; N, 12.44. Found: C, 45.44; H, 4.68; N, 12.22.

EXAMPLE 8

(−)-(3S,4R)-4-(1,1-Dioxo-4-[(thiophen-2-ylmethyl)-amino]-[1,2,5]thiadiazol-3-ylamino]-2,2-dimethyl-6-trifluoromethoxy-chroman-3-ol 2-Thiophenemethylamine (57.1 mg, 0.500 mmol) in acetonitrile (3 mL) is added to a solution of the product of Example 1, Step 2 (0.218 g, 0.500 mmol) in acetonitrile (5 mL). After stirring at room temperature for 48 hours, the solvent is removed and the residue is triturated diethyl ether/hexane to yield 0.226 g (90%) of a white solid: mp 230 (dec); $^1$H NMR (DMSO-D$_6$): δ 8.75 (br s, 1H), 7.53 (d, 1H), 7.27 (s, 1H), 7.22 (s, 1H), 7.18 (d, 1H), 7.04 (t, 1H), 6.90 (d, 1H), 6.00 (br s, 1H), 4.77 (d, 1H), 4.74 (s, 2H), 3.60 (d, 1H), 1.39 (s, 3H), 1.19 (s, 3H); IR (KBr) 3300, 1620 cm$^{-1}$; MS (m/z) 505 (MH$^+$)

Elemental analysis for C$_{19}$H$_{19}$N$_4$S$_2$O$_5$F$_3$: Calc'd: C, 45.23; H, 3.80; N, 11.11. Found: C, 45.46; H, 3.87; N, 10.86.

EXAMPLE 9

(−)-(3S,4R)-4-((1R or 1S)-4-Ethoxy-1-oxo-[1,2,5]thiadiazol-3-ylamino)-2,2-dimethyl-6-trifluromethoxy-chroman-3-ol (3S, 4R)-4-Amino-2,2-dimethyl-6-(trifluoromethoxy)-chroman-3-ol (5.83 g, 21.05 mmol) was stirred with 3,4-diethoxy-1,2,5-thiadiazole-1-oxide [prepared by the method of Algieri et al. *J. Med. Chem.* 1982, 25, 210; (5.00 g, 26.32 mmol)] in ethanol (80 mL) at 80° C. for 18 hour. The mixture was cooled, concentrated, and partitioned between ethyl acetate/water. The organic phase was dried (MgSO$_4$) and concentrated to afford a residue which was purified by flash column (1:2 hexane/ethyl acetate) to give 6.39 g (72%) of product as a 1:1 mixture (as determined by HPLC and $^1$H NMR) of diastereomers (epimeric at sulfur). The diastereomers were separated by HPLC (Waters Prep 500, 2% methanol in dichloromethane using silica gel cartridge, UV=254 nm) to give 3.04 g (34%) of the less polar diastereomer (higher Rf) as a white foam: mp 95°–99° C., $^1$H NMR (DMSO-D$_6$): δ 8.97 (d, 1H), 7.21 (dd, 1H), 7.11 (d, 1H), 6.89 (d, 1H), 5.77 (d, 1H), 4.80 (t, 1H), 4.51 (m, 2H), 3.84 (m, 1H), 1.39 (t and s, 6H), 1.16 (s, 3H); IR (KBr): 3400, 1595 cm$^{-1}$; MS (m/z) 422 (MH$^+$, 100%), 177 (12); [E]$_D^{25}$ = −85.6.

Elemental analysis for C$_{16}$H$_{18}$N$_3$O$_5$SF$_3$: Calc'd: C, 45.60; H, 4.31; N, 9.97. Found: C, 45.94; H, 4.45; N, 9.67.

In addition, 2.40 g (27%) of the more polar diastereomer (lower Rf) was collected as a white foam: mp 96°–101° C.; $^1$H NMR (DMSO-D$_6$): δ 8.87 (d, 1H), 7.22 (d, 1H), 7.15 (dd, 1H), 6.86 (d, 1H), 5.84 (d, 1H), 4.81 (t, 1H), 4.47 (m, 2H), 3.84 (m, 1H), 1.39 (t and s, 6H), 1.16 (s, 3H); IR (KBr): 3400, 1595 cm$^{-1}$; MS (m/z) 422 (MH$^+$, 100%); [α]$_D^{25}$ = −116.3.

Elemental analysis for C$_{16}$H$_{18}$N$_3$O$_5$SF$_3$: Calc'd: C, 45.60; H, 4.31; N, 9.97. Found: C, 45.90; H, 4.43; N, 9.64.

EXAMPLE 10

(−)-(3S,4R)-2,2-Dimethyl-4-(4-methylamino-1-oxo-[1,2,5]thiadiazol-3-ylamino)-6-trifluoromethoxy-chroman-3-ol Methylamine gas was bubbled through a solution of the product of Example 9 (more polar diastereomer; 0.22 g, 0.523 mmol) in acetonitrile (6 mL) at 0° C. for 10 minutes. The mixture was stirred at 25° C. for 1 hour and concentrated. The resulting residue was triturated to a white solid with diethyl ether, hexane, and petroleum ether. Yield: 0.17 g (81%) of compound as a 9:1 mixture of epimers at sulfur as indicated by HPLC and $^1$H NMR. This ratio, however, shifts to a 3:2 equilibrium mixture in solution: mp 249°–250° C. (dec); $^1$H NMR (DMSO-D$_6$): δ 8.35 (m, 1H), 7.99 (m, 1H), 7.19 (m, 2H), 6.91 (d, 1H), 5.90 (d, 1H), 4.84 (m, 1H), 3.64 (m, 1H), 2.94 (s, 3H), 1.40 (s, 3H), 1.20 (s, 3H); IR (KBr): 3300 cm$^{-1}$; MS (m/z) 407 (MH$^+$, 100%), 229 (30), 201 (40); [α]$_D^{25}$ = −75.7 (THF).

Elemental analysis for C$_{15}$H$_{17}$N$_4$O$_4$SF$_3$: Calc'd: C, 44.33; H, 4.22; N, 13.79. Found: C, 44.32; H, 4.07; N, 13.54.

EXAMPLE 11

(Trans)-3-(4-amino-1,1-dioxo-[1,2,5]thiadiazol-3-ylamino)-1,1-dimethyl

Step 1) Preparation of (trans)-3-Amino-1,1-dimethyl-5-nitro-indan-2-ol 3,3-Dimethyl-1,2-epoxy-6-nitroindan [prepared by the method of Buckle et al. *J. Med. Chem.* 1991, 34, 919; (12.94 g, 63.12 mmol)] was dissolved in ethanol (100 mL) and then diluted with aqueous 30% ammonium hydroxide (900 mL). The mixture was stoppered and stirred vigorously for 24 hours at 20° C. The reaction mixture was concentrated to ¼ volume and then extracted with ethyl acetate and dichloromethane. The combined organic phase was washed with water and concentrated. Product precipitated out (6.81 g) and was filtered off. The mother liquor afforded starting epoxide which was re-subjected to the above reaction conditions. An additional 1.02 g of product was obtained.

Total yield: 7.83 g (56%) of amino alcohol as a white solid: mp 148°–151° C. (dec); $^1$H NMR (DMSO-D$_6$): δ 8.15 (s, 1H), 8.05 (d, 1H), 7.42 (d, 1H), 5.43 (br s, 1H), 3.90 (d, 1H), 3.50 (br d, 1H), 2.10 (br s, 2H), 1.30 (s, 3H), 1.00 (s, 3H).

Step 2) Preparation of (trans)-3-(4-Ethoxy-1,1-dioxo-[1,2,5]thiadiazol-3ylamino)-1,1-dimethyl-5-nitro-indan-2-ol The above amino alcohol (1.00 g, 4.505 mmol) and the product of Example 1, Step 2 (0.974 g, 4.73 mmol) were refluxed together in acetonitrile (20 mL) for 18 hours and then stirred at 25° C. for 24 hours. The solvent was removed and the residue was partitioned between ethyl acetate and brine. The organic phase was dried, decolorized, and concentrated to afford 1.44 g (84%) of product as a white foam which was used directly: $^1$H NMR (DMSO-D$_6$): δ 9.65 (d, 1H), 8.24 (dd, 1H), 8.17 (d, 1H), 7.54 (d, 1H), 5.80 (d, 1H), 5.05 (t, 1H), 4.50 (m, 2H), 4.15 (dd, 1H), 1.45 (t, 3H), 1.34 (s, 3H), 1.08 (s, 3H).

Step 3) Preparation of (trans)-3-(4-Amino-1,1-dioxo-[1,2,5]thiadiazol-3-ylamino)-1,1-dimethyl-5-nitro-indan-2-ol Ammonia gas was bubbled through a solution of the above thiadiazole derivative (0.300 g, 0.78 mmol) in acetonitrile (10 mL) at 0° C. for 10 minutes. The mixture was stirred for 1 hour at 25° C., then concentrated to afford a residue which was triturated with ethyl acetate/hexane and filtered. The solid was recrystallized from dimethyl sulfoxide/water to give 0.15 g (54%) of product as a white solid: mp 325°–327° C. (dec); $^1$H NMR (DMSO-D$_6$): δ 9.03 (br d, 2H), 8.21 (dd, 1H), 8.17 (d, 1H), 7.90 (br s, 1H), 7.59 (d, 1H), 5.92 (d, 1H), 5.10 (t, 1H), 3.94 (m, 1H), 1.36 (s, 3H), 1.10 (s, 3H); IR (KBr): 3380, 3180, 1640 cm$^{-1}$; MS (m/z) 354 (MH+, 100%).

Elemental analysis for C$_{13}$H$_{15}$N$_5$O$_5$S: Calc'd: C, 44.19; H, 4.28; N, 19.82. Found: C, 44.25, H, 4.25; N, 19.20.

EXAMPLE 12

(Trans)-1,1-dimethyl-3-(4-methylamino-1,1-dioxo-[1,2,5]thiadiazol-3-ylamino)-5-nitro-indan-2-ol In a method similar to that in Example 11, Step 3, the product of Example 11, Step 2 was converted to the title compound using methylamine gas to afford 0.17 g (59%) of product as a white solid: mp 315°–317° C. (dec); $^1$H NMR (DMSO-D$_6$): δ 8.97 (br d, 1H), 8.57 (br d, 1H), 8.21 (dd, 1H), 8.17 (d, 1H), 7.58 (d, 1H), 5.90 (br d, 1H), 5.11 (m, 1H), 3.90 (d, 1H), 2.97 (s, 3H), 1.36 (s, 3H), 1.09 (s, 3H); IR (KBr): 3340 cm$^{-1}$; MS (m/z) 368 (MH+, 100%).

Elemental analysis for C$_{14}$H$_{17}$H$_5$O$_5$S: Calc'd: C, 45.77; H, 4.66; N, 19.06. Found: C, 45.73; H, 4.69; N, 18.34.

EXAMPLE 13

(−)-(3S,4R)-2,2-Dimethyl-4-(4-pyrrolidino-1,1-dioxo-[1,2,5]thiadiazol-3-ylamino)-6-(trifluoromethoxy)-chroman-3-ol In a method similar to Example 5, the product of Example 1, Step 2 (0.218 g, 0.500 mmol) was converted to the title compound with pyrrolidine (0.053 g, 0.780 mmol) in 1 hour to give 0.34 g of product which was purified by flash column (3:2 hexane/ethyl acetate) to afford 0.17 (74%) of white solid after recrystallization: mp 243°–245° C.; $^1$H NMR (DMSO-D$_6$): δ 7.74 (d, 1H), 7.29 (d, 1H), 7.18 (dd, 1H), 6.89 (d, 1H), 5.81 (d, 1H), 4.94 (t, 1H), 4.00 (m, 1H), 3.87 (m, 2H), 3.57 (m, 2H), 2.10–1.90 (m, 4H), 1.41 (s, 3H), 1.17 (s, 3H); IR (KBr): 3350, 1595 cm$^{-1}$; MS (m/z) 463 (MH+, 100%); $[α]_D^{25} = -75.5$ (THF).

Elemental analysis for C$_{18}$H$_{21}$N$_4$O$_5$SF$_3$: Calc'd: C, 46.75; H, 4.58; N, 12.12. Found: C, 46.38; H, 4.69; N, 12.23.

EXAMPLE 14

(−)-(3S,4R)-2,2-Dimethyl-4-(4-dimethylamino-1-oxo-[1,2,5]thiadiazol-3-ylamino)-6-trifluoromethoxy-chroman-3-ol In a method similar to that in Example 10, the product of Example 9 (more polar diastereomer; 0.230 g, 0.546 mmol) was converted to the title compound (4:1 mixture of epimers at sulfur) using dimethylamine gas to afford 0.15 g (66%) of product as a white solid: mp 131°–135° C. (dec); $^1$H NMR (DMSO-D$_6$): δ 7.74 (br d, 1H), 7.16 (m, 2H), 6.87 (m, 1H), 5.82 (br d, 1H), 4.95 (m, 1H), 3.94 (m, 1H), 3.20 (s, 6H), 1.41 (s, 3H), 1.17 (s, 3H); IR (KBr): 3360 cm$^{-1}$; MS (m/z) 421 (MH+, 45%), 371 (55); $[α]_D^{25} = -55.3$ (THF).

Elemental analysis for C$_{16}$H$_{19}$N$_4$O$_4$SF$_3$: Calc'd: C, 45.71; H, 4.56; N, 13.33. Found: C, 45.94; H, 4.61; N, 13.06.

The smooth muscle relaxing activity of the compounds of this invention was established in accordance with standard pharmaceutically accepted test procedures in representative compounds as follows:

Sprague-Dawley rats (150–200 g) are rendered unconscious by CO$_2$ asphyxiation and then euthanized by cervical dislocation. The bladder is removed into warm (37 deg.C.) physiological salt solution (PSS) of the following composition (mM): NaCl, 118.4; KCl, 4.7; CaCl$_2$, 2.5; MgSO$_4$, 4.7; H$_2$O, 1.2; NaHCO$_3$, 24.9; KH$_2$PO$_4$, 1.2; glucose, 11.1; EDTA, 0.023; gassed with 95% O$_2$; 2/5% CO$_2$; pH 7.4. The bladder is opened and then cut into strips 1–2 mm in width and 7–10 mm in length. The strips are subsequently suspended in a 10 ml tissue bath under an initial resting tension of 1.5 g. The strips are held in place by two surgical clips one of which is attached to fixed hook while the other is attached to an isometric force transducer. The preparations, which usually exhibit small spontaneous contractions, are allowed to recover for a period of 1 hour prior to a challenge with 0.1 uM carbachol. The carbachol is then washed out and the tissue allowed to relax to its resting level of activity. Following an additional 30 minute period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last min of a 30 min challenge.

Isometric force developed by the bladder strips is measured using a concentration required to elicit 50% inhibition of pre-drug contractile activity (IC$_{50}$ concentration) is calculated from this concentration-response curve. The maximum percentage inhibition of contractile activity evoked by a test compound is also recorded for concentrations of test compound ≤ or equal to 30 uM.

The results of this study demonstrated activity in the representative compounds shown in Table I:

TABLE I

| Inhibition of Contractions in Isolated Rat Bladder Strips | | | |
|---|---|---|---|
| Compound | n | IC$_{50}$ | Inhibition of Force (%) at (X) μM |
| Example 1 | 2 | — | 37% ↑ inc (30) |
| Example 2 | 3 | — | 33 (30) |
| Example 3 | 3 | 4.8 | 95 (30) |

Hence, the compounds of this invention have a pronounced effect on smooth muscle contractility and thus are useful in the treatment of hypertension, urinary incontinence, irritable bladder and bowel disease, asthma, stroke and similar disease states as mentioned above, which are amenable to treatment with potassium channel activating compounds by administration, orally or parenterally, to a patient in need thereof.

Applicable solid carriers for the compounds of this invention include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection or as aerosols for inhalation therapy. Sterile solutions can also be administered intravenously. Oral administration may be in either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific situation must be subjectively determined by the attending physician. The variables involved include the specific disease state, route of administration and the size, age and response pattern of the patient.

What is claimed is:

1. A compound of the formula:

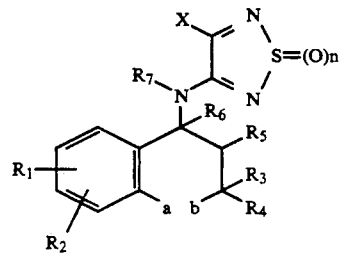

wherein:
R$_1$ and R$_2$, independent from each other, are selected from the following: C$_{1-6}$ perfluoroalkoxy, C$_{1-6}$ perfluoralkyl, C$_{1-6}$ alkyl, C$_{1-6}$ alkoxy, hydroxyl, C$_{2-6}$ alkoxycarbonyl, nitro, cyano, halogeno, C$_{1-6}$ alkylsulfonamido, C$_{1-6}$ perfluoroalkylsulfonamido, amino, C$_{2-6}$ alkanoylamino, C$_{2-6}$ perfluoroalkanoylamino, C$_{1-12}$ mono- or di-alkylamino, C$_{1-6}$ alkylsulfonyl, C$_{6-12}$ arylsulfonyl, carboxyl, C$_{2-12}$ mono- or di-alkylcarbamoyl, or hydrogen;

a and b together form an —O— linkage or a direct bond;

R$_3$ and R$_4$, independent from each other, are C$_{1-6}$ alkyl when a and b form an —O— linkage or, H or C$_{1-6}$ alkyl when a and b form a direct bond;

either R$_5$ is hydrogen, hydroxyl, C$_{26}$ alkanoyloxy, C$_{7-12}$ aroyloxy, carbamoyloxy, formyloxy, C$_{2-6}$ alkoxycarbonyloxy, mono or di C$_{2-12}$ alkylcarbamoyloxy, and R$_6$ is hydrogen, or R$_5$ and R$_6$ together are a bond;

R$_7$ is hydrogen, C$_{1-6}$ alkyl, C$_{1-6}$ alkanocarbonyl, or C$_{1-6}$ alkanosulfonyl;

X is selected from the following:
—NR$_8$R$_9$, wherein R$_8$ and R$_9$, independent from each other are hydrogen, C$_{1-6}$ alkyl, C$_{2-6}$ alkylcarbonyl, C$_{7-12}$ arylalkyl, thienylmethyl, pyridinylmethyl, piperazinylmethyl, or pyrimidinylmethyl, or R$_8$ and R$_9$ taken together are polymethylene of 3-10 carbon atoms or R$_8$ and R$_9$ taken with the nitrogen atom to which they are attached complete a piperazine, morpholine, pyrrolidine, pyrrolidinone, imidazole, imidazolone, piperidine or piperidinone ring structure;

or —OR$_{10}$, wherein R$_{10}$ is hydrogen, C$_{1-6}$ alkyl or C$_{2-6}$ alkylcarbonyl; and n is an integer from 0-2;

or a pharmaceutically acceptable salt thereof.

2. A compound of claim 1 in which:
R$_1$ and R$_2$, independent from each other, are trifluoromethoxy, methoxy, nitro, cyano, chloro, bromo, fluoro, trifluoromethyl, methanesulfonamido, C$_{1-3}$ alkyl, C$_{1-6}$ mono or di-alkylamino, acetamido, trifluoroacetamido, or trifluoromethanesulfonamido;

a and b together form an —O— linkage or a direct bond;

$R_3$ and $R_4$ are methyl when a and b form an —O— linkage or, H or methyl when a and b form a direct bond;

either $R_5$ is hydrogen, or hydroxyl, and $R_6$ is hydrogen, or $R_5$ and $R_6$ together form a bond;

$R_7$ is hydrogen or methyl;

X is $NR_8R_9$, wherein $R_8$ and $R_9$, independent from each other, are, hydrogen, $C_{1-3}$ alkyl, $C_{7-12}$ arylalkyl or thienylmethyl, or $R_8$ and $R_9$ together are polymethylene of 4 to 6 carbon atoms, or $R_8$ and $R_9$ taken together with the nitrogen atom to which they are attached complete a pyrrolidine, pyrrolidinone, piperazine, piperidine or piperidinone ring structure; and n is an integer from 1–2;

or a pharmaceutically acceptable salt thereof.

3. The compound of claim 1 which is (−)-(3S,4R)-4-(4-ethoxy-1,1-dioxo-[1,2,5]thiadiazol-3-ylamino)-2,2-dimethyl-6-trifluoromethoxy-chroman-3-ol or a pharmaceutically acceptable salt thereof.

4. The compound of claim 1 which is (−)-(3S,4R)-4-(4-amino-1,1-dioxo-[1,2,5]thiadiazol-3-ylamino)-2,2-dimethyl-6-trifluoromethoxy-chroman-3-ol or a pharmaceutically acceptable salt thereof.

5. The compound of claim 1 which is (−)-(3S,4R)-2,2-dimethyl-4-(4-methylamino-1,1-dioxo-[1,2,5]thiadiazol-3-ylamino)-6-trifluoromethoxy-chroman-3-ol or a pharmaceutically acceptaable salt thereof.

6. The compound of claim 1 which is (−)-(3S,4R)-2,2-dimethyl-4-(4-dimethylamino-1,1-dioxo-[1,2,5]-thiadiazol-3-ylamino)-6-trifluoromethoxy-chroman-3-ol or a pharmaceutically acceptable salt thereof.

7. The compound of claim 1 which is (−)-(3S,4R)-4-(4-benzylamino-1,1-dioxo-[1,2,5]thiadiazol-3-ylamino)-2,2-dimethyl-6-trifluoromethoxy-chroman-3-ol or a pharmaceutically acceptable salt thereof.

8. The compound of claim 1 which is (−)-(3S,4R)-4-[1,1-dioxo-4-(4-trifluoromethylbenzylamino)-[1,2,5]thiadiazol-3-ylamino]-2,2-dimethyl-6-trifluoromethoxy-chroman-3-ol or a pharmaceutically acceptable salt thereof.

9. The compound of claim 1 which is (−)-(3S,4R)-4-[4-(1-methylethylamino)-1,1-dioxo-[1,2,5]thiadiazol-3-ylamino]2,2-dimethyl-6-(trifluoromethoxy)-chroman-3-ol or a pharmaceutically acceptable salt thereof.

10. The compound of claim 1 which is (−)-(3S,4R)-4-(1,1-Dioxo-4-[(thiophen-2-ylmethyl)-amino]-[1,2,5,]thiadiazol-3-ylamino]-2,2-dimethyl-6-trifluoromethoxy-chroman-3-ol or a pharmaceutically acceptable salt thereof.

11. The compounds of claim 1 which are (−)-(3S,4R)-4-((1R and 1S)-4-ethoxy-1-oxo-[1,2,5]thiadiazol-3-ylamino)-2,2-dimethyl-6-trifluoromethoxy-chroman-3-ol or a pharmaceutically acceptable salt thereof.

12. The compound of claim 1 which is (−)-(3S,4R)-2,2-Dimethyl-4-(4-methylamino-1-oxo-[1,2,5]thiadiazol-3-ylamino)-6-trifluoromethoxy-chroman-3-ol or a pharmaceutically acceptable salt thereof.

13. The compound of claim 1 which is (trans)-3-(4-amino-1,1-dioxo-[1,2,5]thiadiazol-3-ylamino)-1,1-dimethyl-5-nitro-indan-2-ol or a pharmaceutically acceptable salt thereof.

14. The compound of claim 1 which is (trans)-1,1-Dimethyl-3-(4-methylamino-1,1-dioxo-[1,2,5]thiadiazol-3-ylamino)-5-nitro-indan-2-ol or a pharmaceutically acceptable salt thereof.

15. The compound of claim 1 which is (−)-(3S,4R)-2,2-Dimethyl-4-(4-pyrrolidino-1,1-dioxo-[1,2,5]thiadiazol-3-ylamino)-6-(trifluoromethoxy)-chroman-3-ol or a pharmaceutically acceptable salt thereof.

16. The compound of claim 1 which is (−)-(3S,4R)-2,2-dimethyl-4-(4-dimethylamino-1-oxo-[1,2,5]thiadiazol-3-ylamino)-6-trifluoromethoxy-chroman-3-ol, or a pharmaceutically acceptable salt thereof.

17. A pharmaceutical composition comprising a sufficient amount of a compound to activate potassium channels in a mammal in need thereof and a pharmaceutically acceptable carrier, wherein said compound is of the formula:

wherein:

$R_1$ and $R_2$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, $C_{2-12}$ mono- or di-alkylcarbamoyl, or hydrogen;

a and b together form an —O— linkage or a direct bond;

$R_3$ and $R_4$, independent from each other, are $C_{1-6}$ alkyl when a and b form an —O— linkage or, H or $C_{1-6}$ alkyl when a and b form a direct bond;

either $R_5$ is hydrogen, hydroxyl, $C_{2-6}$ alkanoyloxy, $C_{7-12}$ aroyloxy, carbamoyloxy, formyloxy, $C_{2-6}$ alkoxycarbonyloxy, mono or di $C_{2-12}$ alkylcarbamoyloxy, and $R_6$ is hydrogen, or $R_5$ and $R_6$ together are a bond;

$R_7$ is hydrogen, $C_{1-6}$ alkyl, $C_{1-6}$ alkanocarbonyl, or $C_{1-6}$ alkanosulfonyl;

X is selected from the following:
—$NR_8R_9$, wherein $R_8$ and $R_9$, independent from each other are hydrogen, $C_{1-6}$ alkyl, $C_{2-6}$ alkylcarbonyl, $C_{7-12}$ arylalkyl, thienylmethyl, pyridinylmethyl, piperazinylmethyl, or pyrimidinylmethyl, or $R_8$ and $R_9$ taken together are polymethylene of 3–10 carbon atoms or $R_8$ and $R_9$ taken with the nitrogen atom to which they are attached complete a piperazine, morpholine, pyrrolidine, pyrrolidinone, imidazole, imidazolone, piperidine or piperidinone ring structure;

or —$OR_{10}$, wherein $R_{10}$ is hydrogen, $C_{1-6}$ alkyl or $C_{2-6}$ alkylcarbonyl;

and n is an integer from 0–2;

or a pharmaceutically acceptable salt thereof.

18. A pharmaceutical composition comprising an antihypertensive amount of a compound of the formula:

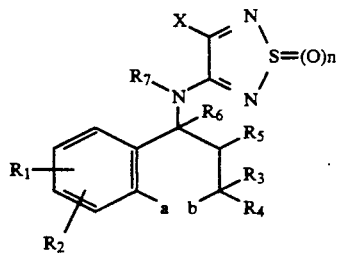

wherein:

R$_1$ and R$_2$, independent from each other, are selected from the following: C$_{1-6}$ perfluoroalkoxy, C$_{1-6}$ perfluoroalkyl, C$_{1-6}$ alkyl, C$_{1-6}$ alkoxy, hydroxyl, C$_{2-6}$ alkoxycarbonyl, nitro, cyano, halogeno, C$_{1-6}$ alkylsulfonamido, C$_{1-6}$ perfluoroalkylsulfonamido, amino, C$_{2-6}$ alkanoylamino, C$_{2-6}$ perfluoroalkanoylamino, C$_{1-12}$ mono- or di-alkylamino, C$_{1-6}$ alkylsulfonyl, C$_{6-12}$ arylsulfonyl, carboxyl, C$_{2-12}$ mono- or di-alkylcarbamoyl, or hydrogen;

a and b together form an —O— linkage or a direct bond;

R$_3$ and R$_4$, independent from each other, are C$_{1-6}$ alkyl when a and b form an —O— linkage or, H or C$_{1-6}$ alkyl when a and b form a direct bond;

either R$_5$ is hydrogen, hydroxyl, C$_{2-6}$ alkanoyloxy, C$_{7-12}$ aroyloxy, carbamoyloxy, formyloxy, C$_{2-6}$ alkoxycarbonyloxy, mono or di C$_{2-12}$ alkylcarbamoyloxy, and R$_6$ is hydrogen, or R$_5$ and R$_6$ together are a bond;

R$_7$ is hydrogen, C$_{1-6}$ alkyl, C$_{1-6}$ alkanocarbonyl, or C$_{1-6}$ alkanosulfonyl;

X is selected from the following:
—NR$_8$R$_9$, wherein R$_8$ and R$_9$, independent from each other are hydrogen, C$_{1-6}$ alkyl, C$_{2-6}$ alkylcarbonyl, C$_{7-12}$ arylalkyl, thienylmethyl, pyridinylmethyl, piperazinylmethyl, or pyrimidinylmethyl, or R$_8$ and R$_9$ taken together are polymethylene of 3–10 carbon atoms or R$_8$ and R$_9$ taken with the nitrogen atom to which they are attached complete a piperazine, morpholine, pyrrolidine, pyrrolidinone, imidazole, imidazolone, piperidine or piperidinone ring structure;
or —OR$_{10}$, wherein R$_{10}$ is hydrogen, C$_{1-6}$ alkyl or C$_{2-6}$ alkylcarbonyl;

and n is an integer from 0–2;
or a pharmaceutically acceptable carrier thereof.

* * * * *